US012622782B2

(12) United States Patent
Kuetting et al.

(10) Patent No.: US 12,622,782 B2
(45) Date of Patent: May 12, 2026

(54) PROSTHETIC DEVICE FOR IMPLANTATION IN THE AORTIC VALVE REGION OF A HEART

(71) Applicant: NVT AG, Morges (CH)

(72) Inventors: Maximilian Kuetting, Gaertringen (DE); Steffen Westermann, Herrenberg (DE)

(73) Assignee: NVT AG, Morges (CH)

( * ) Notice: Subject to any disclaimer, the term of this patent is extended or adjusted under 35 U.S.C. 154(b) by 718 days.

(21) Appl. No.: 18/050,437

(22) Filed: Oct. 27, 2022

(65) Prior Publication Data

US 2023/0068697 A1       Mar. 2, 2023

Related U.S. Application Data

(63) Continuation of application No. PCT/EP2021/060330, filed on Apr. 21, 2021.

(30) Foreign Application Priority Data

Apr. 29, 2020       (DE) ...................... 10 2020 111 681.0

(51) Int. Cl.
*A61F 2/24*          (2006.01)

(52) U.S. Cl.
CPC ............. *A61F 2/246* (2013.01); *A61F 2/2412* (2013.01)

(58) Field of Classification Search
CPC .......... A61F 2/24; A61F 2/246; A61F 2/2418; A61F 2/2412; A61F 2/243; A61F 2/2427;
(Continued)

(56) References Cited

U.S. PATENT DOCUMENTS 9,839,513 B2     12/2017  Essinger et al.
11,147,667 B2 *  10/2021  Yohanan ............... A61F 2/2418
(Continued)

FOREIGN PATENT DOCUMENTS

EP            2149349        2/2010
WO      WO 2009/045331        4/2009
(Continued)

OTHER PUBLICATIONS

International Search report for International Application No. PCT/EP2021/060330, mailed Aug. 2, 2021, in 12 pages.
(Continued)

*Primary Examiner* — Seema Mathew
(74) *Attorney, Agent, or Firm* — Jason H. Vick; Amped IP LLC

(57)          ABSTRACT

The present invention relates to a prosthetic device for deployment in the native aortic valve region of a heart, comprising a tubular spacer element, the spacer element being configured for placement within the native aortic valve region of a heart without contacting to the native aortic annulus; the prosthetic device further comprises at least one anchoring element designed for anchoring the prosthetic device within the heart, and at least one connecting element, coupling the spacer element to the at least one anchoring element; in the prosthetic device, the tubular spacer element further comprises a coaptation skirt element being connected to the outer surface of the spacer element, such, that the coaptation skirt element is inflatable during diastole.

12 Claims, 7 Drawing Sheets

(58) Field of Classification Search

CPC .. A61F 2/2409; A61F 2230/0065; A61F 2/86;
A61F 2/07

See application file for complete search history.

(56) References Cited

U.S. PATENT DOCUMENTS

| | | | | |
|---|---|---|---|---|
| 12,514,699 | B2 * | 1/2026 | Morin | A61F 2/2412 |
| 2014/0277417 | A1 * | 9/2014 | Schraut | A61F 2/2418 |
| | | | | 623/2.17 |
| 2014/0350660 | A1 * | 11/2014 | Cocks | A61F 2/2418 |
| | | | | 623/1.16 |
| 2025/0161035 | A1 * | 5/2025 | Levi | A61F 2/2418 |
| 2025/0248810 | A1 * | 8/2025 | Shitrit | A61F 2/2418 |

FOREIGN PATENT DOCUMENTS

| | | | | |
|---|---|---|---|---|
| WO | WO-2012048035 A2 * | 4/2012 | .......... | A61F 2/2433 |
| WO | WO 2013/178335 | 12/2013 | | |
| WO | WO 2021/219453 | 11/2021 | | |

OTHER PUBLICATIONS

Written Opinion for International Application No. PCT/EP2021/060330, mailed Aug. 2, 2021.

International Preliminary Report on Patentability for International Application No. PCT/EP2021/060330, mailed Nov. 10, 2022.

* cited by examiner

PROSTHETIC DEVICE FOR IMPLANTATION IN THE AORTIC VALVE REGION OF A HEART

CROSS REFERENCES TO RELATED APPLICATIONS

This application is a continuation of International Patent Application No. PCT/EP2021/060330, filed on Apr. 21, 2021, which claims priority to German patent application DE102020111681.0, filed on Apr. 29, 2020. The entire contents of each of these priority applications is incorporated herein by reference.

BACKGROUND

The present invention concerns an implantable prosthetic device for implantation in the native aortic valve region of a heart, in particular for treating aortic valve regurgitation, as well as the use of such a device for treating diseased or otherwise dysfunctional aortic valves.

Nowadays, prosthetic aortic valve devices are used as a possible treatment of aortic valve insufficiency, also referred to as aortic regurgitation. Such prosthetic valves are delivered by traditional surgical implantation methods, or by less invasive percutaneous catheter or minimally invasive methods.

The mammalian heart comprises four chambers, i.e. two atria, which are the filling chambers, and two ventricles, which are the pumping chambers. In a mammalian heart, there are four heart valves present which normally allow blood to flow in only one direction through the heart, whereby a heart valve opens or closes depending on the differential blood pressure on each side.

The four main valves in the heart are the mitral valve, representing a bicuspid valve, and the tricuspid valve, which are between the upper atria and the lower ventricles, respectively, and thus are called atrioventricular (AV) valves. Further, there are the aortic valve and the pulmonary valve which are in the arteries leaving the heart. The mitral valve and the aortic valve are in the left heart and the tricuspid valve and the pulmonary valve are in the right heart.

The valves incorporate leaflets or cusps, wherein each valve has three cusps, except for the mitral valve, which only has two.

The aortic valve, which normally has three cusps, is situated between the left ventricle and the aorta. The aortic valve is the last structure in the heart the blood travels through before stopping the flow through the systemic circulation. The aortic valve—like to pulmonary valve—is also called "semilunar valve", permitting blood to be forced into the aorta, and prevents backflow from the aorta into the ventricle during diastole. During ventricular systole, pressure rises in the left ventricle and when it is greater than the pressure in the aorta, the aortic valve opens, allowing blood to exit the left ventricle into the aorta. When ventricular systole ends, pressure in the left ventricle rapidly drops and the pressure in the aorta forces aortic valve to close.

Several different kinds of valve disorders are known, such as stenosis, which occurs when a heart valve doesn't fully open due to stiff or fused leaflets preventing them from opening properly, or prolapse, where the valve flaps do not close smoothly or evenly but collapse backwards into the heart chamber they are supposed to be sealing off.

Valve regurgitation (backward flow) is also a common problem, and occurs when a heart valve doesn't close tightly, as a consequence of which the valve does not seal and blood leaks backwards across the valve. This condition—also called valvular insufficiency—reduces the heart's pumping efficiency: When the heart contracts blood is pumped forward in the proper direction but is also forced backwards through the damaged valve. As the leak worsens, the heart has to work harder to make up for the leaky valve and less blood may flow to the rest of the body. Depending on which valve is affected, the condition is called tricuspid regurgitation, pulmonary regurgitation, mitral regurgitation, or aortic regurgitation.

Aortic regurgitation, i.e. the abnormal leaking of blood from the aorta through the aortic valve and into the left ventricle when the left ventricle contracts, is a common valvular abnormality. A dysfunction of the valve results in left ventricular hypertrophy and heart failure. Common causes of aortic regurgitation include vasodilation of the aorta, previous rheumatic fever, infection such as infective endocarditis, degeneration of the aortic valve, and Marfan's syndrome. Aortic stenosis can also be caused by rheumatic fever and degenerative calcification. The most common congenital abnormality of the heart is the bicuspid aortic valve, i.e. the fusion of two cusps.

Surgical intervention is recommended for symptomatic severe aortic regurgitation or asymptomatic severe aortic regurgitation with left ventricular dysfunction or enlargement.

Meanwhile, as already mentioned at the outset, aortic valve repair and replacement has also been achieved using minimally invasive procedures. The desire for less invasive approaches is linked with the fact that a significant proportion of patients, especially elderly persons or those with significant comorbidities or severe left ventricular dysfunction, are not referred for (open heart) surgery.

Various percutaneous technologies have emerged and are at different stages of development. Current percutaneous technologies for aortic valve repair or replacement are, e.g., percutaneous aortic valve replacement, enhanced aortic coaptation, percutaneous aortic valvuloplasty, and percutaneous aortic annuloplasty (sub-commissural annuloplasty).

However, the different percutaneous repair approaches do still not offer the same degree of efficacy as a surgical repair of the aortic valve.

While the technology of percutaneous aortic valve replacement to treat aortic regurgitation is a possible alternative in a selected group of patients with a low probability of successful repair, the challenges of this technique are high: the aortic annulus is often much bigger than usually, and different anchoring designs might be required for different aortic regurgitation etiologies. Further, paravalvular leaks might pose problems.

E.g., WO 2013/178335 A1 discloses an implantable device for improving or rectifying a heart valve insufficiency and comprises a contact strip attached to a closure element, which contact strip forms a loop in the atrium thus contacting the inner wall of the heart and attaching the device therein.

SUMMARY

In view of the above, there still is the need for a heart valve prosthesis by means of which heart valve regurgitation can be efficiently treated, while at the same time traumatic impact on the heart is minimized.

According to the invention, this and other objects is solved by a prosthetic device for implanting at the native aortic valve region of a heart, the native aortic valve having a native annulus and native valve leaflets, the prosthetic device comprising a tubular spacer element comprising an outer surface, an inner surface, a length, a proximal inflow end, a distal outflow end and a lumen defined there between, the spacer element being configured for placement within the native aortic valve region of a heart without contacting to the native aortic annulus, and comprising a valve element being attached within the lumen to the spacer element's inner surface at the proximal inflow end; at least one anchoring element, wherein the anchoring element is spatially separate from the tubular spacer element, and wherein the anchoring element is capable to anchor the prosthetic device within the native aortic valve region of a heart, and at least one connecting element coupling the spacer element to the at least one anchoring element, such, that spacer element is co-axially aligned and suspended inside the native aortic valve without contact to the aortic annulus; in the prosthetic device according to the invention, the tubular spacer element comprises a coaptation skirt element, having a distal end and proximal end, the coaptation skirt element being connected, via its distal outflow end and its proximal inflow end, to the outer surface of the spacer element, such, that the coaptation skirt element is inflatable during diastole.

The present invention also concerns the use of the device in the treatment of aortic valve regurgitation of a patient in need thereof, preferably a human, as well as a method for treating aortic valve regurgitation of a patient in need thereof, preferably a human.

With the prosthetic device according to the invention, the space left by malcoaptation of the native aortic leaflets can filled out, and, thus, aortic regurgitation can be reduced or even eliminated when placing the device according to the invention inside the annulus of a native aortic valve at the respective coaptation line.

With the dimensions of the tubular spacer of the device according to the invention being smaller than a native aortic annulus, the disclosed prosthetic device allows emission to the aorta and body extremities through the device and alongside the device during systole, and thus minimizes the gradient between the left ventricle and the aorta.

In a healthy heart, when the left atrium chamber contracts in late diastole, it sends blood to the larger, lower left ventricle chamber. When the lower ventricle chamber is filled and the mitral valve to the left atrium is closed, the ventricle undergoes isovolumetric contraction (contraction of the ventricle while the mitral valve is closed), marking the first stage of systole. The second phase of systole sends blood from the left ventricle to the aorta and body extremities.

As mentioned above in the introductory part, the human aortic valve contains three leaflets, or cusps, poles, or flaps of connective tissue that passively move apart or mate together in response to the forces imposed by the flow of blood. Accordingly, with the term "poles of the valve" three alignments are meant, with 120 degrees apart from one another in the circumferential edge of the stent, where the commissure of the valve leaflets are sutured to.

As also described in the introducing section above, when aortic valve closure is impaired and the leaflets do not seal properly, blood leaks and flows backwards from the aorta into the left ventricle, which may increase left ventricle end-diastolic pressure which may eventually leads to elevated left atrial and pulmonary pressure with resulting pulmonary edema, as well as decreased coronary perfusion gradients that potentially can cause myocardial ischemia and even sudden cardiac death.

With the device according to the invention, a unidirectional flow is created, preventing flow from the aorta to the left ventricle in diastole and permitting flow from the ventricle to the aorta in systole: The leaflets of the native aortic valve coapt/abut against the inflated coaptation skirt element attached to tubular spacer of the prosthetic device according to the invention, thus sealing the aortic annulus during diastole and recreating the valvular function of the structure. The space left between the malcoapting aortic leaflets can, thus, be filled out without expanding the space and without forcing the not properly closed valve even further open.

With the anchoring element of the prosthetic device of the invention, the device as a whole gets secured within the aortic valve region of a heart, while at the same time the coaptation of the native aortic valve against the inflatable coaptation skirt attached to the tubular spacer element is guaranteed: Via the anchoring element, the tubular spacer element, which carries the valve element, gets suspended inside the native aortic valve without contacting the aortic annulus. Thus, the tubular spacer element has a size and shape that is suitable for guaranteeing this function, i.e. to "float free" inside the native aortic valve. This suspension is provided via the anchoring element anchored in the aortic valve region and the connecting elements, connecting the tubular spacer element with the anchoring element.

Also, with the coaptation skirt element provided with the prosthetic device according to the invention, and its specific attachment to the tubular spacer element, such, that it gets "inflated" during diastole, a coaptation is provided.

With a "coaptation skirt element", an sheet-like element for at least partially covering the outer surface of the tubular spacer is meant, that is circumferentially "wrapped around" the outer surface of the tubular spacer element, thus defining a distal end and proximal end of the coaptation skirt element; solely via its proximal and distal end, the coaptation skirt element is fixedly attached, e.g. sewn or otherwise mounted, to the outer surface of the tubular spacer, such, that the portion between the proximal and distal end of the coaptation skirt element is not fixedly attached to the outer surface of the tubular spacer element.

With "inflated" and "inflatable" as used herein in view of the coaptation skirt element, an attachment of the coaptation skirt element to the tubular spacer is meant, such, that the coaptation skirt element, which is only attached to the tubular spacer via its distal end and its proximal end,—or rather its non-attached portion—can get detached from the outer surface during diastole in a balloon-like fashion. The native valve can, thus, coapt against the inflated skirt, thus, closing the valve.

Presently, the expression "adapts to the coaptation zone of the native aortic valve" or "coapts against" in view of the tubular spacer element—or rather in view of the coaptation skirt element attached thereto—means, that the tubular spacer together with the coaptation skirt element attached thereto, has a shape and design such that it fits into and fills out the space left by the not properly closing leaflets of the native, malfunctioning aortic valve, without the tubular spacer contacting the native aortic annulus.

According to the invention, the tubular spacer element, the anchoring element and the connecting elements form three separate portions. In particular, the at least one anchoring element and the spacer element are separate parts and the anchoring element does not form direct part of the spacer element, both portions only being connected via at least one connecting element.

Further, the expression "proximal end" of the main body is used to designate the inflow section of the lumen of the device's main body, i.e. the end of its lumen where blood enters to flow into the aorta. Accordingly, the expression "distal end" of the lumen designates the outflow lumen end, i.e. the end where the blood exits the lumen.

With the prosthetic device of the invention, during diastole and upon flow from the aorta, the valve element within the spacer element closes, leading to a pressure build up inside the spacer, which in turn inflates the loose coaptation skirt element on the outer surface of the spacer element, causing the coaptation skirt element to form contact with the leaflets of the malfunctioning native aortic valve, filling in the coaptation gap and recreating sufficiency of valve closure, thus preventing backflow.

According to a preferred embodiment, in the prosthetic device of the invention, the coaptation skirt element, starting from the proximal inflow end of the spacer element, circumferentially covers the spacer element's outer surface up to 30%, 40%, 50%, 60%, 70%, 80%, 90%, or up to 100%.

With these embodiments, the coaptation skirt element is attached, via its proximal end, to outer surface of the proximal inflow end of the spacer element, and circumferentially covers the outer surface of the spacer element with the given percentages. E.g., when the coaptation skirt element circumferentially covers 100% of the outer surface of the spacer element, the distal end of the coaptation skirt element is attached to the outer surface of the distal outflow end of the spacer element.

According to another preferred embodiment, in the prosthetic device of the invention, the coaptation skirt element comprises or consists of a material selected from the group of biocompatible artificial material or biocompatible natural material, and in particular is selected from human or animal pericardium, polytetrafluoroethylene (PTFE), polyurethane and polyester.

Generally, the size of the coaptation skirt element is such, that it can be circumferentially "wrapped"/guided around the tubular spacer element, circumferentially covering its outer surface, being attached—via its proximal end—to the proximal inflow end, and, thus, the covering "starting from" the proximal inflow end towards the distal outflow end up to 100%.

Preferably, in the device according to the invention, the tubular spacer element comprises or consists of a tubular stent frame and has a cross section that is selected from substantially round, oval, and triangular. Thus, according to a preferred embodiment, the tubular spacer has a cylindrical shape.

The overall shape of the tubular spacer element of the device according to the invention is tubular, either with a consistent diameter of the cross section over the whole length or with a diameter of the cross section at the proximal end being larger than the diameter of the cross-section of the distal end, thus conferring the main body a substantially cone-shaped or convex form.

Presently, and as generally understood, the term "stent frame" is meant to comprise a cylindrical, tubular, or otherwise tubular shaped radially-expandable metal frame or body, and, thus, comprises any device or structure that adds rigidity, expansion force, or support to a prosthesis. A stent frame may also consist of substantially hollow expandable structures, which can be filled or inflated to reach their functional shape.

The metal frame of the tubular spacer element's stent frame can be laser cut or woven or braided or knitted or comprise an otherwise interconnected metal mesh.

According to an embodiment, in the device according to the invention the stent frame is preferably made of a shape-memory material, preferably Ninitol. Nitinol has been proven as suitable for implantable medical devices and used in different medical appliances.

According to a preferred embodiment, the stent frame is comprised of or consists of a series of singular stent elements or wire framework of filaments, made of a self-expanding material.

According to a preferred embodiment, the stent frame may also be comprised of single metal rings forming a metal mesh, the rings meandering circumferentially and being disposed successively in the tubular spacer element's longitudinal axis/direction, wherein the metal rings have a Z-shaped profile with pointed arches pointing alternately toward the proximal end and distal end of the device.

The valve carried in the tubular spacer element of the prosthetic device can be created/taken from human or animal donors. They can be created/taken, e.g., from pericardium of human or any mammal, or from native leaflets from the heart or veins, or from any other biological material suitable for the intended purpose. Generally speaking, such valves are also called biological or tissue valves—as contrary to mechanical valves.

In the device according to the invention, the valve may comprise flexible materials, or a rigid mechanical valve mechanism is used, e.g. monoleaflet, bileaflet, ballcage, caged disc. Flexible materials include aortic valve leaflets harvested from animals, animal pericardial tissue, tissue engineered material, harvested human pericardial tissue or synthetic materials. The design may use one, two, three, or more individual leaflets of equal or different sizes.

Presently, the expressions "substantially cylindrical" or "substantially round, oval" presently mean any three-dimensional form that has a certain length, and that has a substantially round cross section, wherein also forms are comprised the cross sections of which are, e.g., an ellipse, parabola, or hyperbola, and wherein the cross-section does not necessarily need to have a regular circumference, but also includes irregular circumferences, as long as the substantially cylindrical form of the valve carrying stent-portion is retained. Also, with the expression "substantially cylindrical" forms are comprised which conform or substantially conform to the treated valve anatomic annulus shape.

Similar, the expression "substantially continuous", e.g. in connection with the diameter of the substantially cylindrical shape of the tubular spacer element means that, generally, the diameter of the cylindrical form is about the same over its length, wherein it will be clear to one skilled in the art that there can be minor or slight variations in diameter due to manufacturing issues.

The components of the device, i.e. the tubular spacer element, the anchoring element and the connecting elements, can be variously sized in terms of length, diameter, etc., as suitable for an intended use and as depending on the respective condition and shape and dimension/shape of the patient's heart, while at the same time comprising the features of the device as claimed.

According to a preferred embodiment of the invention, the tubular spacer's stent frame of the prosthetic device is self-expanding, wherein the device is configured, such, that it is convertible from a compressed state for introducing the device into a heart of a mammal to an expanded state within the heart.

According to a preferred embodiment, the anchoring element of the prosthetic device of the invention consists of a cylindrical stent element.

The "cylindrical stent element"—as the stent frame as discussed above—is meant to comprise a substantially cylindrical/tubular radially-expandable metal frame or body, and, thus, comprises any device or structure that has rigidity and expansion force suitable for anchoring the prosthetic device in the aortic valve region of a heart. Accordingly, the stent element can be laser cut or woven or braided or knitted or comprise an otherwise interconnected metal mesh. The stent element can be made of a shape-memory material, preferably Ninitol.

According to a preferred embodiment, the stent element is comprised of or consists of one stent ring or more stent rings interconnected with one another, or otherwise of a framework/metal mesh of filaments, made of a self-expanding material.

According to a preferred embodiment, the stent element may also be comprised of single metal rings forming a metal mesh, the rings meandering circumferentially and being disposed successively in the tubular spacer element's longitudinal axis/direction, wherein the metal rings have a Z-shaped profile with pointed arches pointing alternately toward the proximal end and distal end of the device.

Also, according to a preferred embodiment, the anchoring element, on its outer and/or inner surface, may be covered with any suitable biocomaptible material.

In a preferred embodiment of the prosthetic device of the invention, the anchoring element consists of a cylindrical stent element, and the at least one connecting element consists of one or more singular non-tubular, straight flexible connecting element, the connecting element comprising a first end, a second end and a length extending there between, wherein the connecting element, via its respective first end is coupled to the spacer element, and, via its respective second end, is coupled to the anchoring element, wherein the length of the connecting elements is such, that when the anchoring element is placed downstream of the coronary arteries, preferably in the ascending aorta, the spacer element is suspended within the native aortic valve region of the heart without contacting to the native aortic annulus.

With this embodiment, the anchoring element and the spacer element are—via the connecting elements—spaced apart from one another, such, that the anchoring element is anchored in downstream of the coronary arteries; as a consequence, the spacer element gets suspended in and freely floats inside the native aortic valve. The coronary arteries exit the aorta just above the level of the aortic valve. There are two coronary arteries in the body, the right coronary artery having its origin in the right coronary cusp and the left coronary artery having its origin in the left coronary cusp. Accordingly, with "downstream" generally the direction of the blood flow is meant. Thus, with "downstream of the coronary arteries", it is meant that the anchoring element is placed within the ascending aorta downstream of the aortic valve's cusps; via the connecting elements, the spacer element is suspended inside the annulus without contacting the native annulus.

The connecting elements are preferably flexible, such, that they allow for tilting of the spacer element in respect to the anchoring element, while maintaining their axial length; thus, preferably, the connecting elements are not axially compressible, but bendable.

Also, the connecting elements, in this embodiment, need to have a certain length providing for the distance between the anchoring element and the spacer element, as well as providing a co-axial alignment of the spacer element inside the annulus of the native aortic valve.

Accordingly, the term "straight" in respect of the connecting elements means any lengthy bar- or ligament-like structure the length of which is longer than its width. In some embodiments, the connecting means can be a wire, a bar, a ligament, a thread, or other, and by made from any inert material of sufficient strength generally used in the medical field.

In this connection, a "bar" element or "ligament" element or means is any lengthy structure of sufficient rigidity and flexibility for being coupled, via its one end, to the device according to the invention, and, via its second end, to a structure of the heart and/or to another anchoring element, e.g. a plug. The lengthy structure/bar/ligament element can be of any material suitable for these purposes, and is preferably of an inert, substantially rigid material, such as, metals, e.g. Nitinol, stainless steel, Titanium, polymers, e.g. polyether ether ketone (PEEK), polyoxymethylene (POM), polyether (PE), polyamide (PA), polytetrafluoroethylene (PTFE), which materials may also be reinforced by fibres to improve stability), ceramics, materials of animal or human origin or generally synthetic materials. The structures may also be substantially hollow structures, which are inflatable or fillable to attain their stability. They may also be combinations of the aforementioned. To promote the biocompatibility, the surface of the structures may be coated or otherwise treated.

According to another embodiment of the prosthetic device of the invention, the anchoring element consists of a cylindrical stent element, and the at least one connecting element consists of one or more singular non-tubular, curved flexible connecting element, the connecting element comprising a first end, a second end and a length extending there between, wherein the connecting element via its respective first end is coupled to the spacer element, and, via its respective second end, is coupled to the anchoring element, wherein the length and shape of the connecting elements is such, that when the anchoring element is placed in the aortic root, the spacer element is suspended within the native aortic valve region of the heart without contacting to the native aortic annulus.

In this embodiment, the anchoring element is placed within the aortic root, and suspends—via the curved bent connecting elements—the spacer element inside the native aortic annulus. The anchoring element and the spacer element are, again, co-axially aligned.

According to another embodiment of the prosthetic device of the invention, the at least one connecting elements consist of one or more U-shaped lengthy attachment arm elements, the attachment arm elements comprising a first end, a second end and a length extending there between, wherein the attachment arm elements, via its respective first end is coupled to the spacer element, and, at its respective second end, comprises the at least one anchoring element, wherein the anchoring element consists of attachment means for anchoring the device in tissue surrounding the native aortic annulus, the attachment means being selected from one or more of a hook, a spike or an arrow.

With this embodiment, also a suspension of the spacer element within the native valve region—without contact to the native annulus—is achieved: The anchoring elements, i.e. the attachment means like hooks, spikes arrows anchor, are inserted/hooked into the tissue of the aortic root, and the U-shaped connecting means connect the attachment means with the tubular spacer such, that the tubular spacer is freely floating within the native aortic valve.

According to a preferred embodiment, the prosthetic device of the invention comprises a combination of one or more of the anchoring elements as defined above.

As mentioned above, the invention also concerns the use of the prosthetic device of the invention and as defined and described above and in the accompanying figures in treating aortic valve regurgitation in a patient.

Also, the invention concerns a method for treating aortic valve regurgitation, comprising the steps of providing the prosthetic device of the invention and as described and defined above and in the accompanying figures, and deploying the device in the aortic valve region of a heart in a patient in need thereof in order to replace in its function or support the native aortic valve of said patient.

According to one embodiment, the method comprises the following steps: providing a prosthetic device according to the invention, in particular a prosthetic device which comprises a stent element as anchoring element, introducing the prosthetic device in the aortic valve region of a heart of a patient in need of treatment, deploying the anchoring element downstream of the coronary arteries, preferably in the ascending aorta, thereby suspending the spacer element inside the native aortic annulus.

According to another embodiment, the method comprises the following steps: providing a prosthetic device according to the invention, in particular a prosthetic device which comprises a stent element as anchoring element, introducing the prosthetic device in the aortic valve region of a heart of a patient in need of treatment, deploying the anchoring element in the aortic root behind native aortic leaflets, i.e. upstream of the coronary arteries, thereby suspending the spacer element inside the native aortic annulus.

The patient or subject in need of treating, i.e. the patient or subject suffering from aortic valve regurgitation, is a mammal, preferably a human.

It will be understood that the treatment options provided by the invention are not limited to the aortic valve, but that a device according to the invention may also be used to treat pulmonary valve regurgitation.

The device according to the invention can be either surgically implanted or delivered by transcatheter methods. In the latter case, i.e. with a transcatheter method, the device according to the invention is loaded onto a suitable deployment catheter, there being compressed by a retractable sheath or tube or similar. The deployment catheter is inserted into the heart of a patient whose tricuspid or aortic valve needs replacement or support.

When treating the aortic valve, the deployment catheter having the device according to the invention loaded thereon in a compressed state, is advanced transapically into the left ventricle crossing the aortic valve to the annulus where it is deployed in order to expand the sealing section inside the annulus of the aortic valve at the coaptation line, and the valve-bearing section in the aorta ascendens. Also, the compressed device can be introduced via the femoral vein or Jugular vein into the right atrium, transseptally to the left atrium, across the mitral valve to the left ventricle and to the aorta where it is deployed in order to expand the sealing section in the annulus and the valve-bearing section. Additionally, the compressed device can be introduced via a small surgical thoracotomy into to the pulmonic vein (right, left, inferior or superior pulmonic vein) to the left atrium, across the mitral valve to the left ventricle and to the aorta where it is deployed in order to expand the sealing section in the annulus and the valve-bearing section. Also, the compressed device can be introduced via the femoral artery allowing positioning of the prosthetic device, through the aorta, within the native aortic valve.

Upon correct placement, the sheath or the otherwise compressing means is retracted to release the prosthetic device in a stepwise fashion according to the invention, upon which action the anchoring element of the device can anchor the prosthetic device, and, thus, have the tubular spacer suspended in the native aortic valve region.

Further advantages and features of the invention are set forth in the following description and in the attached figures.

It will be understood that the aforementioned features and the features still to be explained below can be used not only in the respectively specified combination but also in other combinations or on their own, without departing from the scope of the present invention.

BRIEF DESCRIPTION OF THE DRAWINGS

The aforementioned features of the invention and the features still to be explained below are shown in the figures, in which.

EMBODIMENTS

Figure 1A:
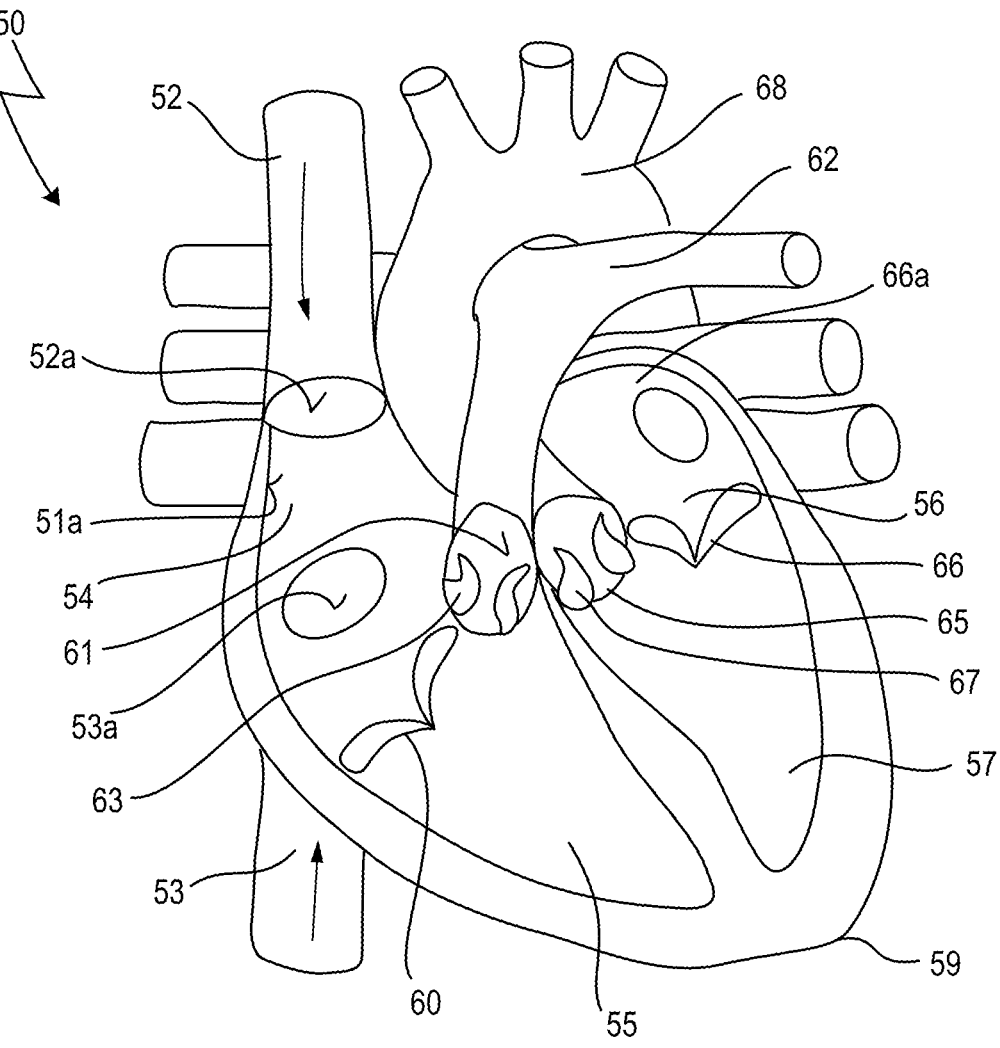
FIG. 1A shows a schematic drawing of a human heart.

In FIG. 1A, a human heart 50 is depicted, having a right atrium 54, a right ventricle 55, a left atrium 56 and a left ventricle 57. Also depicted in FIG. 1 is a portion of the vena cava superior 52, entering the heart 50 via the right atrium 54, and a portion of the vena cava inferior 53.

In more detail, the superior vena cava 52 returns the blood from the upper half of the body, and opens into the upper and back part of the right atrium 54, the direction of its orifice 52a being downward and forward. Its orifice 52a has no valve.

The inferior vena cava 53, which has a larger diameter than the superior vena cava 52, returns the blood from the lower half of the body, and opens into the lowest part of the right atrium 54, its orifice 53a being directed upward and backward, and guarded by a rudimentary valve, the valve of the inferior vena cava (Eustachian valve, not shown).

The right ventricle 55 has a triangular in form, and extends from the right atrium 54 to near the apex 59 of the heart 50.

The right atrioventricular orifice (not depicted in FIG. 1) is the large oval aperture of communication between the right atrium 54 and ventricle 55, and is guarded by the tricuspid valve 60 comprising three triangular cusps or segments or leaflets 64.

The opening 61 of the pulmonary artery 62 is circular in form, and is placed above and to the left of the atrioventricular opening; it is guarded by the pulmonary valves 63.

As discussed above, the function of the tricuspid valve 60 is to prevent back flow of blood into the right atrium 54; arrows 70 and 71 indicate normal blood flow into the right atrium 54.

The left atrium 56 is smaller than the right atrium 54. The left ventricle 57 is longer and more conical in shape than the right ventricle 55. The left atrioventricular opening (mitral orifice, not depicted in FIG. 1) is placed to the left of the aortic orifice 65, and is guarded by the bicuspid or mitral valve 66.

The aortic opening 65 is a circular aperture, in front and to the right of the atrioventricular opening, and its orifice is guarded by the tricuspid aortic valve 67. Reference number 68 designates the aorta.

As mentioned in the introductory part, and generally speaking, the aortic valve 67 helps keep blood flowing in the correct direction through the heart. It separates the heart's left ventricle 57 and the aorta 68 supplying oxygen-rich blood to the body. With each contraction of the ventricle 57, the aortic valve 67 opens and allows blood to flow from the left ventricle 57 into the aorta 68. When the ventricle 57 relaxes, the aortic valve 67 closes to prevent blood from flowing backward into the ventricle 57. When the aortic valve 67 isn't working properly, it can interfere with blood flow and force the heart to work harder to send blood to the rest of the body, causing symptoms like shortness of breath, dizziness, fainting, irregular heartbeat, etc. In aortic valve regurgitation, the aortic valve 67 doesn't close properly, causing blood to flow backward into the left ventricle 57.

Figure 1B:
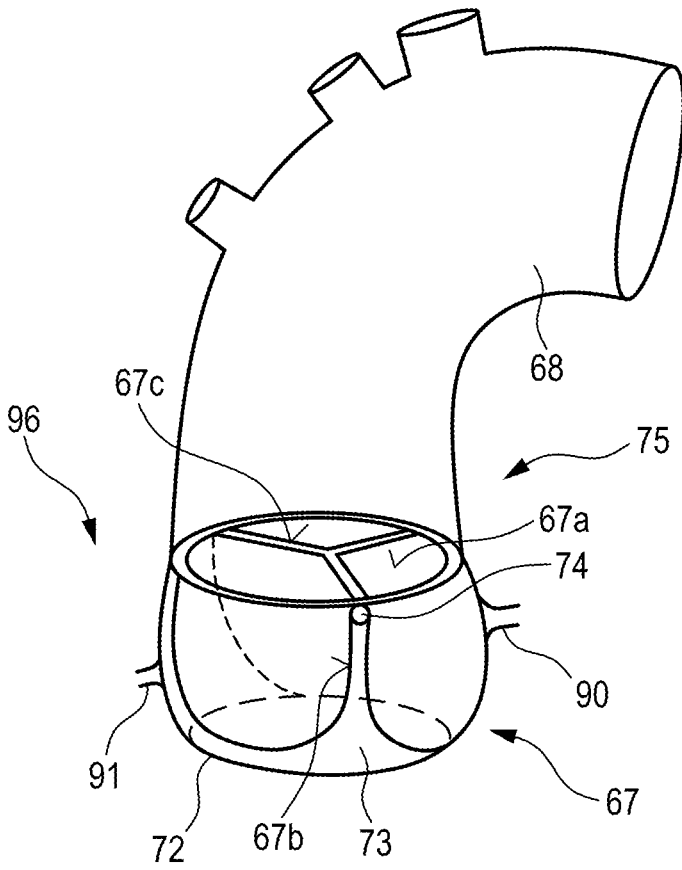
FIG. 1B shows schematic enlarged drawing of an aortic root.

FIG. 1B shows an enlarged drawing of an aortic root 96 of a heart 50. Herein, as generally understood, the term "aortic root" refers to the aortic valve from its position at the left ventricular outlet to its junction with the ascending aorta. Anatomically, this whole structure is the aortic valve. The three leaflets/cusps of the aortic valve 67 are designated with 67a, 67b and 67c, respectively, and the commissure 74 is shown where the cusps 67a and 67b join together. As shown in FIG. 1B, the left the coronary artery 90 and the right coronary artery 91 are branching off supplying the entire heart 50 with oxygen-rich blood. Reference sign 73 designates the interleaflet triangle, and 72 the native annulus.

FIG. 2 shows a schematic drawing of a top view on a malfunctioning aortic valve 67 in the closed status, wherein the three cusps 67a, 67b and 67c of a tricuspid aortic valve 67 are shown. It is to be noted that also bicuspid aortic valves are known, which represent a congenital heart defect. Diseases with only one or four cusps are also known but are rare. Also, there are cases where a bicuspid aortic valve does not close properly, leading—besides of aortic valve regurgitation—also to an enlarged aorta bearing the risk of dissections. Thus, the prosthetic device according to the invention may also be used to treat bicuspid aortic valve diseases.

Figure 2A:
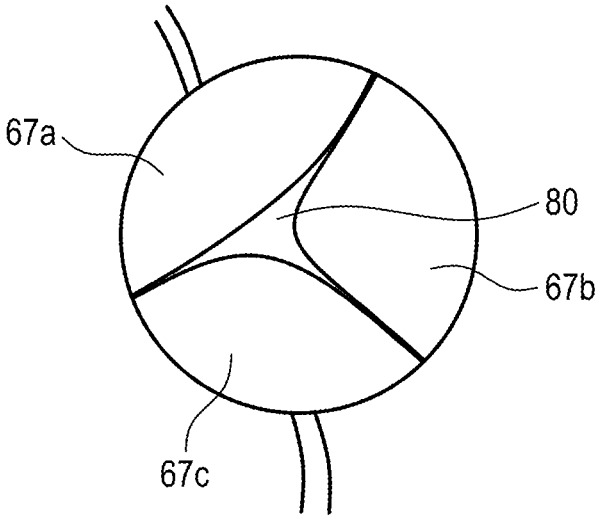
FIG. 2A shows a schematic drawing of the top view of an exemplary malfunctioning aortic valve in closed status without prosthetic device.

As can be seen in FIG. 2A, the native aortic valve 67, or rather its three cusps 67a, 67b, 67c, does/do not close properly, leading to a closure "gap" 80, which in turns allows blood to flow back into the left ventricle during diastole, which is called aortic valve regurgitation. In FIG. 2A, the aortic valve not being supported by a prosthetic device according to the invention.

Figure 2B:
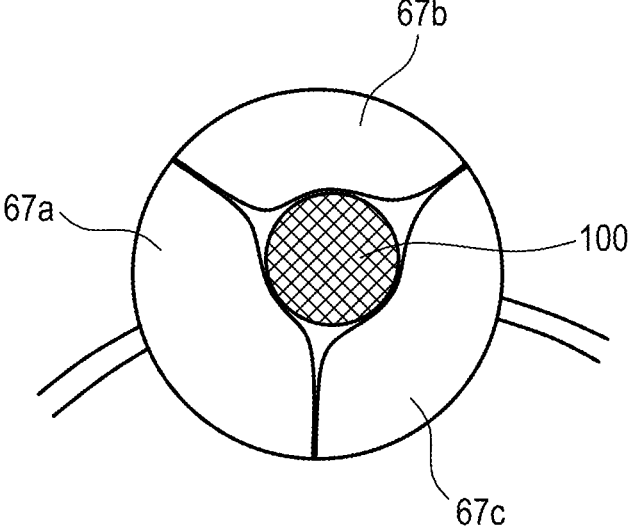
FIG. 2B shows a schematic drawing of the top view of an exemplary malfunctioning aortic valve in closed status with prosthetic device.
Figure 3A:
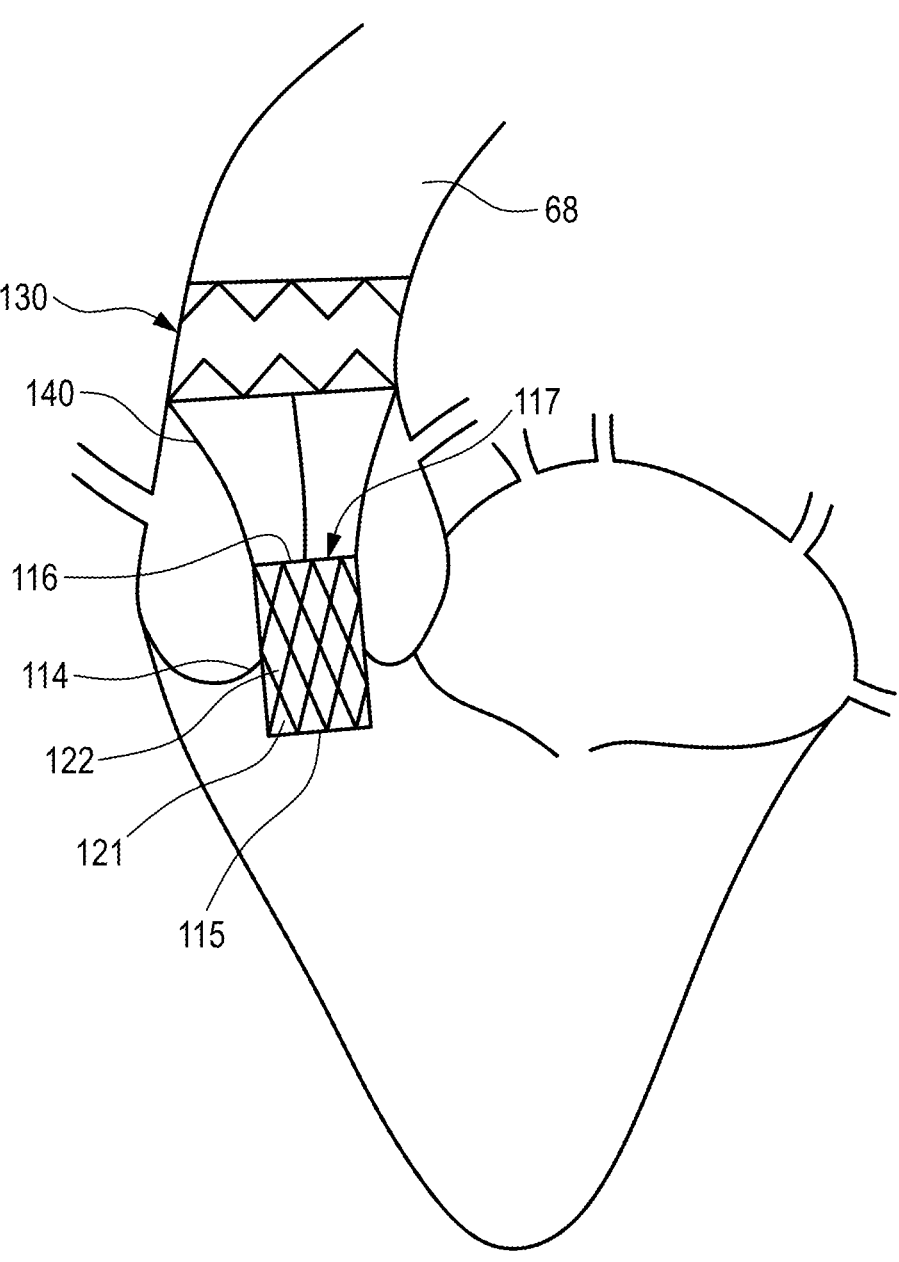
FIG. 3A shows a schematic drawing of an embodiment of the prosthetic device according to the invention, placed in the aortic valve region of a heart.
Figure 3B:
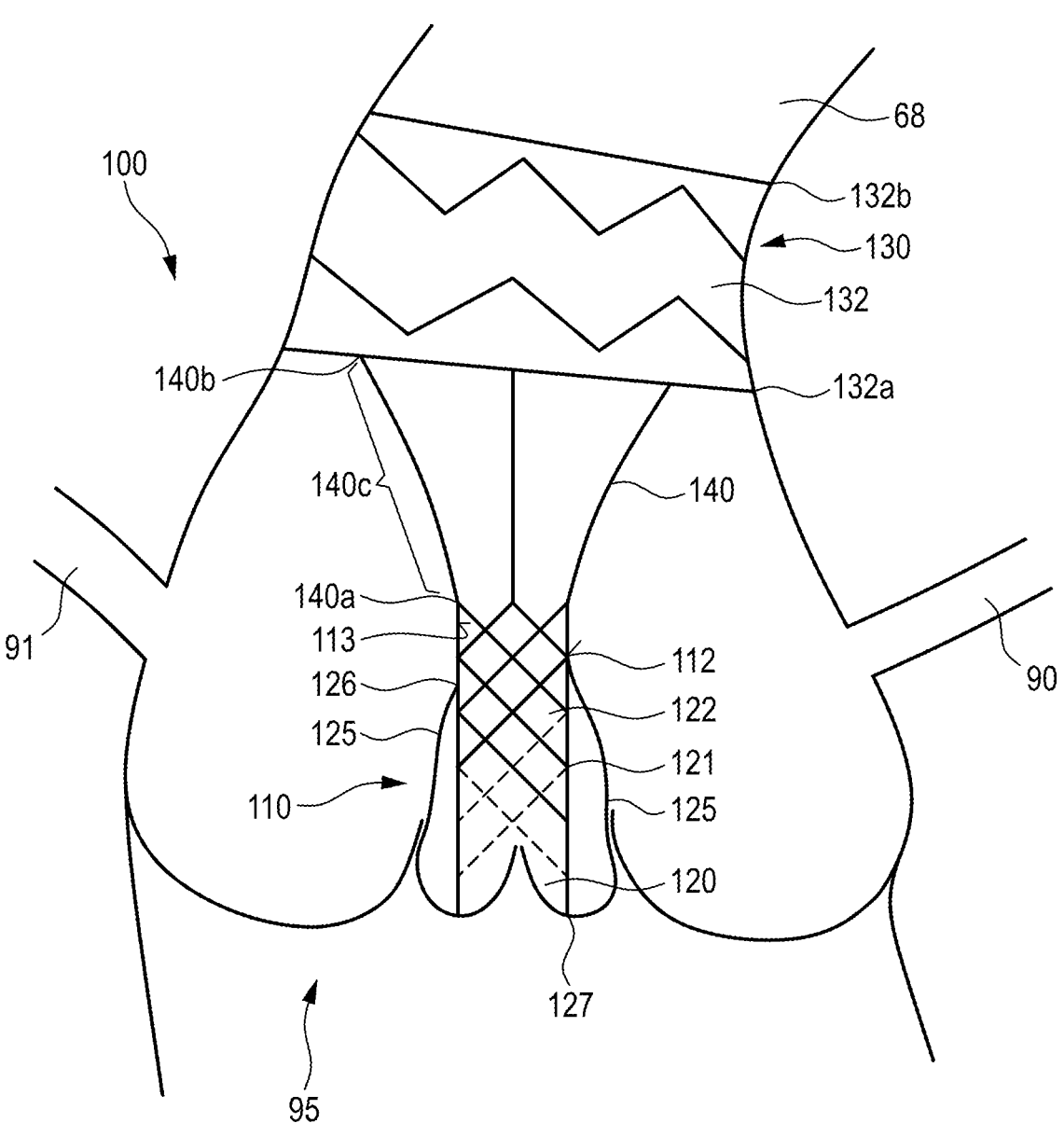
FIG. 3B shows a schematic drawing the placement of FIG. 3A in more detail.
Figure 4:
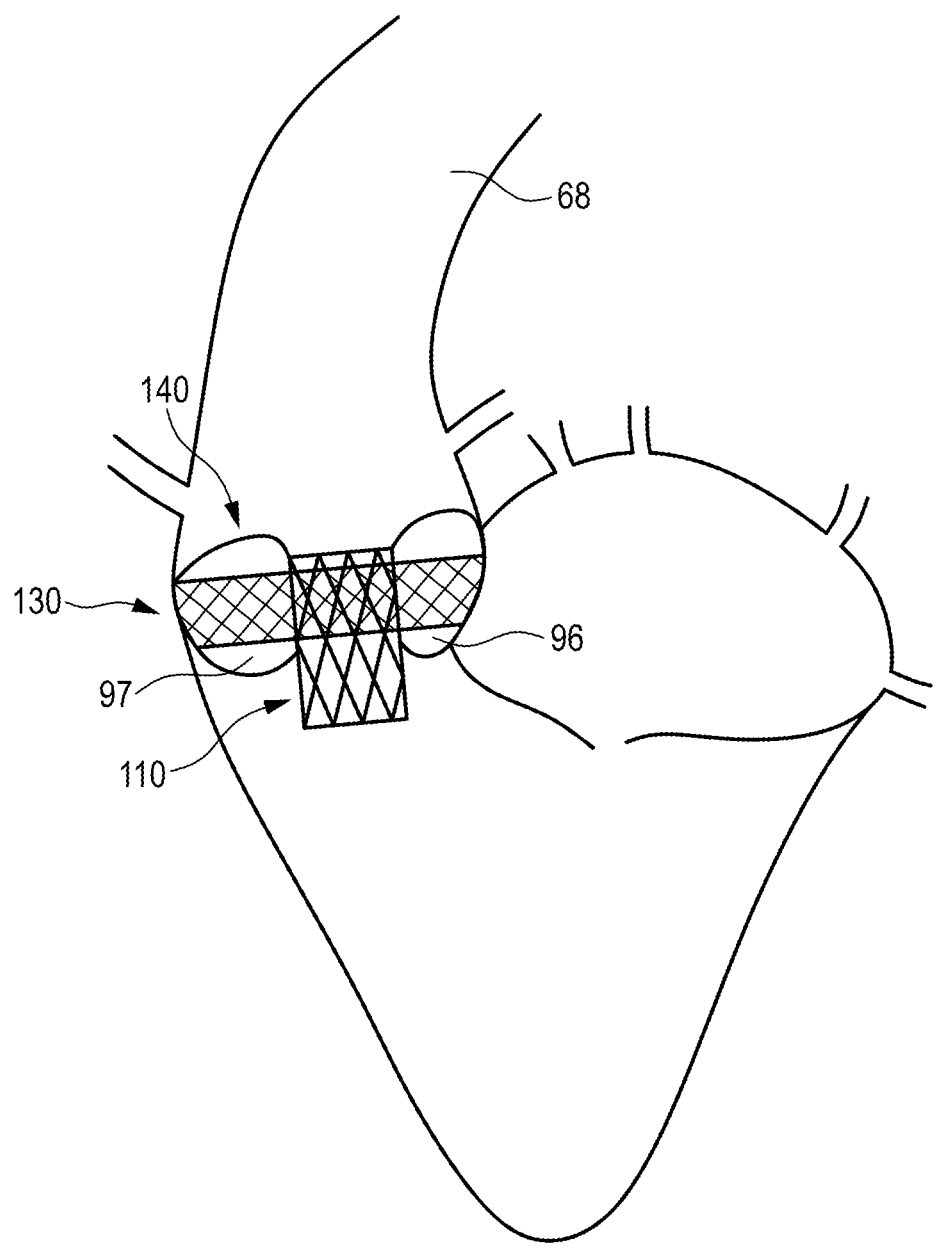
FIG. 4 shows a schematic drawing of another embodiment of the prosthetic device according to the invention, placed in the aortic valve region of a heart.
Figure 5:
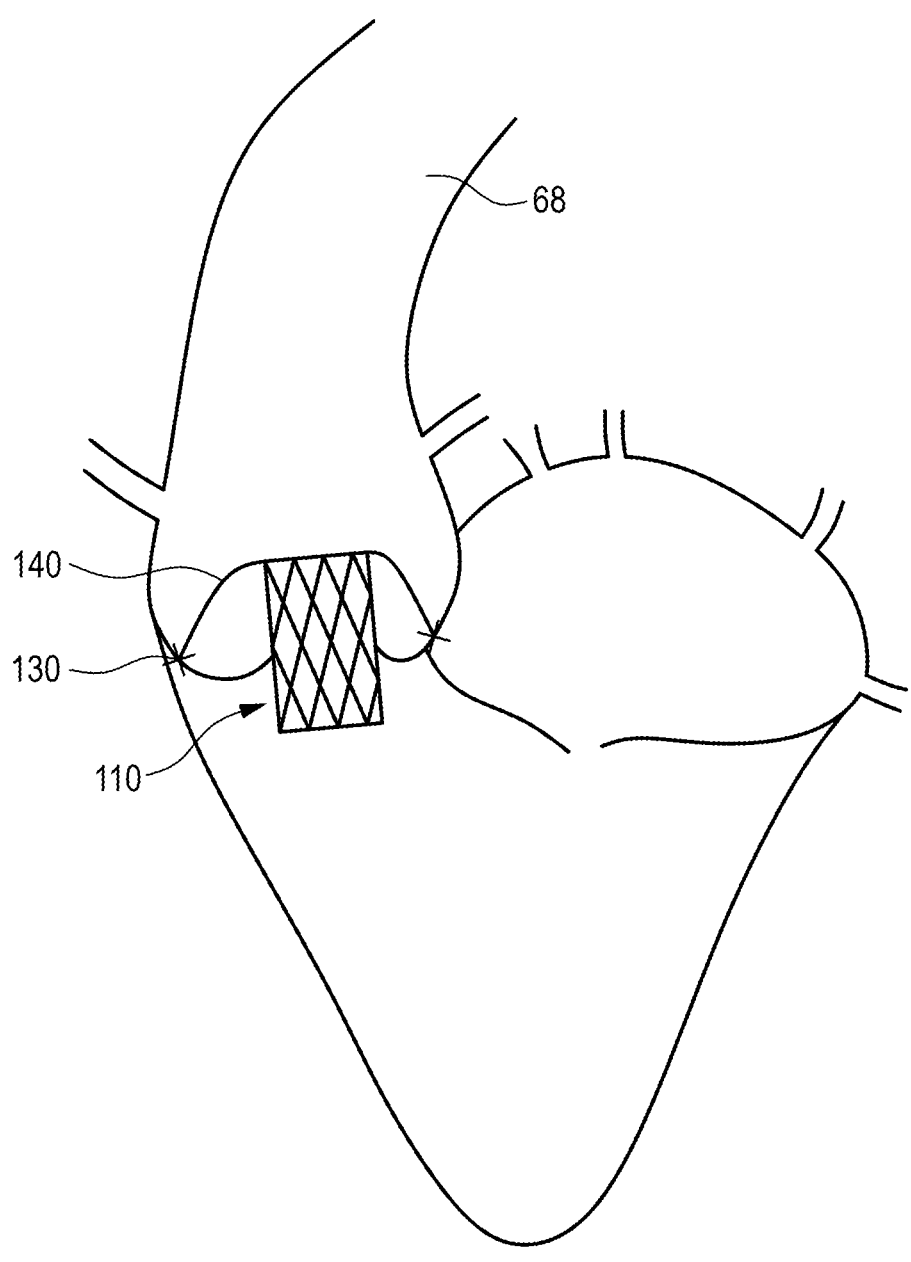
FIG. 5 shows a schematic drawing of yet another embodiment of the prosthetic device according to the invention, placed in the aortic valve region of a heart.

With the device according to the invention, aortic valve regurgitation can be treated, and placement of an exemplary embodiment 100 of the device according to the invention into the diseased native aortic valve of FIG. 2A is depicted in the attached FIG. 2B, which is also shown in more detail in the different embodiments as shown in FIGS. 3 to 5.

In the exemplary embodiments of the prosthetic device 100 according to the invention as shown in FIG. 3, the device 100 is depicted in its expanded state, i.e. the state the device has when implanted into the heart of the patient to be treated. On the other hand, the compressed state is the state the device 100 is in when being loaded onto a transcatheter delivery system compressing the device 100 for introduction via blood vessels of the body.

FIGS. 3 to 5 shows different embodiments for the prosthetic device according to the invention, wherein the same features are designated with the same reference signs in the different embodiments.

The prosthetic device of the invention 100 has a tubular spacer element 110, which is to be placed within the native aortic valve of a patient, without contacting the native annulus. The tubular spacer element 110 comprises an outer surface 112, an inner surface 113, a length 114, a proximal inflow end 115, a distal outflow end 116 and a lumen 117 defined between the inflow end 115 and outflow end 116.

The tubular spacer element further comprises a valve element 120 being attached within the lumen to the spacer element's 110 inner surface 113 at the proximal inflow 115; for sake of clarity of the figures, the valve element 120 is only schematically depicted in FIG. 3B, and has been left out in the other drawings.

As can be seen in the embodiments of FIG. 3, the tubular spacer element 110 has a tubular stent frame 121, made from interconnected wires forming a mesh with diamond-shaped cells 122. The tubular spacer element/the stent frame as depicted in FIG. 3 has a cross section that is substantially round, and, thus the tubular spacer has a cylindrical form, although also other forms like triangular or more egg-shaped could be applied, too.

The tubular spacer element 110, further, has attached hereto, as de-tailed below, a coaptation skirt element 125, which has a distal end 126 and proximal end 127. The coaptation skirt element 125 is circumferentially wrapped around the spacer element 110, and is, via its distal outflow end 126 and its proximal inflow end 127 only, fixedly connected/attached to the outer surface 112 of the spacer element 110. By way of this attachment, i.e. only via its ends to the spacer element 110, the portion of the coaptation skirt element 125 between the ends 126, 127 is can detach during diastole, and, thus is "inflatable" during diastole, as it is shown in FIG. 3B. In that way, the native valve coapts/abuts to the inflated skirt element 125 and not directly to the stent frame of the spacer element 110.

The embodiment shown in FIG. 3, the prosthetic device 100, which is shown enlarged and in more detail in FIG. 3B, further comprises an anchoring element 130, the anchoring element representing a stent element 132, being tubular and having circumferentially meandering stent rings. The stent element has a proximal end 132a, and a distal end 132b, wherein at the proximal end 132a, connecting elements 140 are attached. In FIG. 3, the connecting elements 140 comprise three singular non-tubular, straight flexible connecting elements, each having a first end 140a, a second end 140b and a length 140c extending between the ends 140a, 140b. The connecting elements 140, via their respective first ends 140a are coupled to the spacer element 110, and, via their respective seconds end 140b, are coupled to the anchoring element 130, wherein the length 140c of the connecting elements 140 is such, that when the anchoring element 130 is placed downstream of the coronary arteries 90, 91, the spacer element 110 is suspended within the native aortic valve region 95 of the heart without contacting to the native aortic annulus.

FIG. 4 shows another embodiment of the prosthetic device 100 according to the invention. Here, the anchoring element 130 also consists of a cylindrical stent element 132. The device further comprises three singular non-tubular, curved flexible connecting elements 140, the connecting elements 140 comprising a first end 140a, a second end 140b and a length 140c extending between the ends 104a, 140b. The connecting element s 140, via their respective first ends 140a, are coupled to the spacer element 110, and, via their respective second ends 140b, are coupled to the anchoring element 130. The length 104c and shape of the connecting elements 140 is such, that when the anchoring element 130 is placed in the aortic root 96 behind the native aortic leaflets 97, the spacer element 110 is suspended within the native aortic valve region 95 of the heart without contacting to the native aortic annulus.

FIG. 5 shows yet another embodiment of the prosthetic device according to the invention, also comprising tubular spacer element 110 suspendingly placed in the native aortic valve region without contacting the native aortic annulus. Here, the connecting elements 140 consist of three U-shaped lengthy attachment arm elements 141, the attachment arm elements 141 comprising a first end 141a, a second end 141b and a length 141c extending between the ends 141a, 141b, wherein the attachment arm elements 141, via their respective first ends 141b are coupled to the spacer element 110, and, at their respective second ends 141b, comprise the at least one anchoring element 130. In the embodiment shown in FIG. 3C, the anchoring element 130 consists of attachment means 135 for anchoring the device 100 in tissue surrounding the native aortic annulus, the attachment means 135, in FIG. 3C representing a spike.

What is claimed is:

1. A prosthetic device for deployment in the native aortic valve region of a heart, the native aortic valve region comprising the native aortic valve having a native annulus and native valve leaflets, the prosthetic device comprising:
   a tubular spacer element comprising an outer surface, an inner surface, a length, a proximal inflow end, a distal outflow end and a lumen defined there between, the spacer element being configured for placement within the native aortic valve region of a heart without contacting to the native aortic annulus, and comprising a valve element being attached within the lumen to the spacer element's inner surface at the proximal inflow end;
   at least one anchoring element, wherein the anchoring element is spatially separate from the tubular spacer element, and wherein the anchoring element is designed for and capable to anchor the prosthetic device within the native aortic valve region of a heart; and
   at least one connecting element, coupling the spacer element to the at least one anchoring element, such, that spacer element is co-axially aligned and suspended inside the native aortic valve without contact to the aortic annulus,
   wherein
   the tubular spacer element comprises a coaptation skirt element, having a distal end and proximal end, the coaptation skirt element being attached, solely via its distal outflow end and its proximal inflow end, to the outer surface of the spacer element, such, that the portion between the proximal and distal end of the coaptation skirt element is not fixedly attached to the outer surface of the tubular spacer element, and that the coaptation skirt element is inflatable during diastole, such, that the coaptation skirt element, with the portion not fixedly attached to the outer surface of the spacer element is detached from the outer surface during diastole in a ballon-like fashion.

2. The prosthetic device of claim 1, wherein the coaptation skirt element, starting from the proximal inflow end of the spacer element, circumferentially covers the spacer element's outer surface up to 30%, 40%, 50%, 60%, 70%, 80%, 90%, or up to 100%.

3. The prosthetic device of claim 1, wherein the coaptation skirt element comprises or consists of a material selected from the group of biocompatible artificial material or biocompatible natural material, and in particular is selected from human or animal pericardium, polytetrafluoroethylene (PTFE), polyurethane and polyester.

4. The prosthetic device of claim 1, wherein the tubular spacer element comprises or consists of a tubular stent frame, and has a cross section that is selected from substantially round, oval, and triangular.

5. The prosthetic device of claim 1, wherein the anchoring element consists of a cylindrical stent element.

6. The prosthetic device of claim 1, wherein the anchoring element consists of a cylindrical stent element, and that the at least one connecting element consists of one or more singular non-tubular, straight flexible connecting element, the connecting element comprising a first end, a second end and a length extending there between, wherein the connecting element, via its respective first end is coupled to the spacer element, and, via its respective second end, is coupled to the anchoring element, wherein the length of the connecting elements is such, that when the anchoring element is placed downstream of the coronary arteries, the spacer element is suspended within the native aortic valve region of the heart without contacting to the native aortic annulus.

7. The prosthetic device of claim 1, wherein the anchoring element consists of a cylindrical stent element, and that the at least one connecting element consists of one or more singular non-tubular, curved flexible connecting element, the connecting element comprising a first end, a second end and a length extending there between, wherein the connecting element via its respective first end is coupled to the spacer element, and, via its respective second end, is coupled to the anchoring element, wherein the length and shape of the connecting elements is such, that when the anchoring element is placed in the aortic root, the spacer element is suspended within the native aortic valve region of the heart without contacting to the native aortic annulus.

8. The prosthetic device of claim 1, wherein the at least one connecting elements consist of one or more U-shaped lengthy attachment arm elements, the attachment arm elements comprising a first end, a second end and a length extending there between, wherein the attachment arm elements, via its respective first end is coupled to the spacer element, and, at its respective second end, comprises the at least one anchoring element, wherein the anchoring element consists of attachment means for anchoring the device in tissue surrounding the native aortic annulus, the attachment means being selected from one or more of a hook, a spike or an arrow.

9. The prosthetic device of claim 1, comprising a combination of one or more of the following anchoring elements (i) to (iii):
   (i) an anchoring element consisting of a cylindrical stent element;
   (ii) an anchoring element consisting of a cylindrical stent element, and the at least one connecting element consisting of one or more singular non-tubular, straight flexible connecting element, the connecting element comprising a first end, a second end and a length extending there between, wherein the connecting element, via its respective first end is coupled to the spacer element, and, via its respective second end, is coupled to the anchoring element, wherein the length of the connecting elements is such, that when the anchoring element is placed downstream of the coronary arteries, the spacer element is suspended within the native aortic valve region of the heart without contacting to the native aortic annulus;

(iii) an anchoring element consisting of a cylindrical stent element, and the at least one connecting element consisting of one or more singular non-tubular, curved flexible connecting element, the connecting element comprising a first end, a second end and a length extending there between, wherein the connecting element via its respective first end is coupled to the spacer element, and, via its respective second end, is coupled to the anchoring element, wherein the length and shape of the connecting elements is such, that when the anchoring element is placed in the aortic root, the spacer element is suspended within the native aortic valve region of the heart without contacting to the native aortic annulus.

10. A method for treating aortic valve regurgitation, the method comprising the steps of providing the prosthetic device of claim 1, and deploying the prosthetic device in the aortic valve region of a heart in a patient in need thereof in order to replace in its function or support the native aortic valve of said patient.

11. A method for treating aortic valve regurgitation the method comprising the following steps:

providing the prosthetic device of claim 1, the device comprising a stent element as anchoring element, introducing the prosthetic device in the aortic valve region of a heart of a patient in need of treatment, deploying the anchoring element downstream of the coronary arteries, preferably in the ascending aorta, thereby suspending the spacer element inside the native aortic annulus.

12. A method for treating aortic valve regurgitation the method comprising the following steps:

providing the prosthetic device of claim 1, the prosthetic device comprising a stent element as anchoring element, introducing the prosthetic device in the aortic valve region of a heart of a patient in need of treatment, deploying the anchoring element in the aortic root behind native aortic leaflets, i.e. upstream of the coronary arteries, thereby suspending the spacer element inside the native aortic annulus.

\* \* \* \* \*